United States Patent [19]
Vought

[11] Patent Number: 5,800,483
[45] Date of Patent: Sep. 1, 1998

[54] SYSTEM AND METHOD FOR STERILE SURGICAL-THERMAL DRAPE WITH ACTIVE AIR CIRCULATION

[75] Inventor: Kimber L. Vought, Columbus, Miss.

[73] Assignee: Microtek Medical, Inc., Columbus, Mich.

[21] Appl. No.: 681,267

[22] Filed: Jul. 22, 1996

Related U.S. Application Data

[63] Continuation-in-part of Ser. No. 620,931, Mar. 21, 1996, abandoned.

[51] Int. Cl.⁶ .................................................. A61F 7/00
[52] U.S. Cl. ....................... 607/104; 607/114; 128/849; 128/853
[58] Field of Search ........................ 607/96, 98, 104, 607/108–112, 114, 107; 128/849, 850–854; 126/204; 165/46

[56] References Cited

U.S. PATENT DOCUMENTS

| | | | |
|---|---|---|---|
| 2,602,302 | 7/1952 | Poux | 62/1 |
| 4,026,299 | 5/1977 | Sauder | 607/104 |
| 4,572,188 | 2/1986 | Augustine et al. | 128/380 |
| 4,575,097 | 3/1986 | Brannigan et al. | 128/402 |
| 4,736,088 | 4/1988 | Bart | 219/211 |
| 4,753,241 | 6/1988 | Brannigan et al. | 128/380 |
| 4,765,323 | 8/1988 | Poettgen | 128/132 D |
| 4,807,644 | 2/1989 | Sandhaus | 128/849 |
| 4,886,063 | 12/1989 | Crews | 128/403 |
| 4,889,135 | 12/1989 | Poettgen | 128/849 |
| 4,945,924 | 8/1990 | Poettgen | 128/849 |
| 5,025,777 | 6/1991 | Hardwick | 126/263 |
| 5,125,238 | 6/1992 | Ragan et al. | 62/259.3 |
| 5,184,612 | 2/1993 | Augustine | 128/400 |
| 5,190,032 | 3/1993 | Zacoi | 607/104 |
| 5,246,656 | 9/1993 | Stephenson et al. | 264/153 |
| 5,265,599 | 11/1993 | Stephenson et al. | 607/104 |
| 5,300,098 | 4/1994 | Philipot | 607/96 |
| 5,300,103 | 4/1994 | Stempel et al. | 607/96 |
| 5,304,213 | 4/1994 | Berke et al. | 607/104 |
| 5,304,217 | 4/1994 | Stephenson et al. | 607/114 |
| 5,350,417 | 9/1994 | Augustine | 607/104 |
| 5,360,439 | 11/1994 | Dickerhoff et al. | 607/104 |
| 5,392,847 | 2/1995 | Stephenson | 165/46 |
| 5,405,371 | 4/1995 | Augustine et al. | 607/107 |
| 5,425,975 | 6/1995 | Koiso et al. | 428/74 |
| 5,443,488 | 8/1995 | Namenye et al. | 607/114 X |
| 5,522,871 | 6/1996 | Sternlicht | 128/849 X |
| 5,545,194 | 8/1996 | Augusting | 607/114 X |

FOREIGN PATENT DOCUMENTS

| | | | |
|---|---|---|---|
| 8503216 | 8/1985 | WIPO | A61F 7/00 |
| 9107625 | 5/1991 | WIPO | F24J 1/00 |

*Primary Examiner*—Robert L. Nasser
*Assistant Examiner*—Ryan Carter
*Attorney, Agent, or Firm*—Baker & Botts, L.L.P.

[57] ABSTRACT

A sterile surgical-thermal drape (10) is provided. The sterile surgical-thermal drape (10) includes a sterile surgical drape (12) that maintains a sterile field and a thermal device (14) attached (16) to the sterile surgical drape (12) for regulating the body temperature of a patient (32). The thermal device (14) has an external surface, and is operable to provide convective heating or cooling to a patient.

6 Claims, 6 Drawing Sheets

SYSTEM AND METHOD FOR STERILE SURGICAL-THERMAL DRAPE WITH ACTIVE AIR CIRCULATION

CROSS-REFERENCE TO RELATED APPLICATIONS

This application is a continuation-in-part of U.S. application Ser. No. 08/620,931 (Attorney Docket No. 017109.0263), entitled Sterile Surgical-Thermal Draping System and Method, filed Mar. 21, 1996, now abandoned.

TECHNICAL FIELD OF THE INVENTION

This invention relates in general to the field of surgical drapes, and more particularly to a system and method for a sterile reusable or disposable surgical drape having thermo-regulatory/thermoprotective features.

BACKGROUND OF THE INVENTION

A patient under general anesthesia will undergo several physiological changes that inhibit the body's normal thermo-regulatory capabilities. General anesthesia depresses the function of thermoregulating centers in the hypothalamus, thus resulting in the body's inability to self-regulate body temperature. Infusion of intravenous fluid may contribute to cooling body temperature during surgery because such intravenous fluids absorb heat from the body when they are at a temperature below body temperature. Inspiration of dry anesthesia gases during surgery may also contribute to body temperature cooling during surgery because the dry gas both absorbs heat from the body and because of the cooling action created when water from the body is absorbed by the dry gas. Moreover, during surgery the body cavity may be exposed, which increases the effective surface area of the body and also cools body parts that are normally not exposed to the environment. The incidence of hypothermia occurring after surgery has been estimated to be as great as 60% to 90%.

To prevent hypothermia from occurring, it is necessary to provide active heating to a patient during surgery. One important requirement for any active heating system or method used during surgery is that it maintains a sterile surgical field. Another important requirement for any active heating system or method is that it delivers sufficient heat to the body to prevent the onset of hypothermia.

Although many devices exist that may be used to provide heat or to provide a sterile environment, none of these devices are capable of performing both functions simultaneously.

SUMMARY OF THE INVENTION

Therefore a need has arisen for a sterile surgical-thermal draping system and method that maintains a sterile field during surgery while providing heat to the patient in a manner that is sufficient to prevent the onset of hypothermia.

Accordingly, the present invention provides a sterile reusable or disposable surgical drape with thermo-regulatory/thermoprotective features that substantially eliminate or reduce the disadvantages and problems associated with previously developed surgical drapes and thermo-regulatory/thermoprotective devices.

One aspect of the present invention provides a sterile surgical-thermal drape. The sterile surgical-thermal drape includes a sterile surgical drape that maintains a sterile field and a thermal device attached to the sterile surgical drape for regulating the body temperature of a patient that provides convective heating or cooling to a patient.

Another aspect of the present invention is a thermal drape that includes channels for carrying a hot or cold fluid. A recirculation unit connects to the entrance and exit of the channels. The recirculation unit circulates a hot or cold fluid, such as air, through the channels.

The present invention provides several technical advantages. One important technical advantage of the present invention is that it provides a device that maintains a sterile surgical field while providing sufficient heat to prevent the onset of hypothermia in a patient. A device incorporating concepts of the present invention may be used to controllably provide heat to a patient under anesthesia while maintaining a sterile environment necessary to safely perform surgery.

Another important technical advantage of the present invention is that it provides a method for using a thermal draping system that may be used in conjunction with a sterile surgical drape that does not require the heating or cooling fluid to be exhausted to the environment.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

Figure 1A:
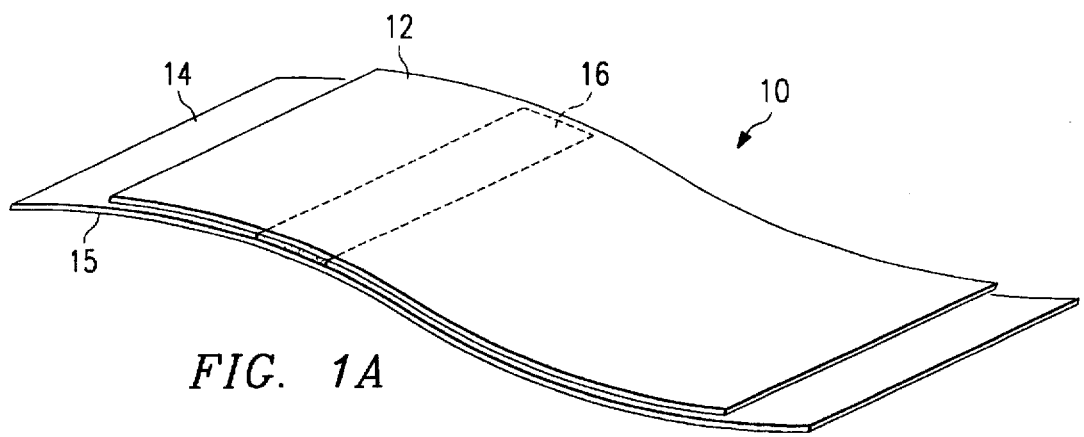
FIGS. 1A and 1B illustrate sterile surgical-thermal drapes embodying concepts of the present invention.

FIG. 1A shows sterile surgical-thermal drape 10 embodying concepts of the present invention. Drape 10 includes flexible sterile surgical drape 12 and flexible thermal device 14. Sterile surgical drape 12 and flexible thermal device 14 may be of identical size, or may have different shapes and sizes as shown in FIG. 1A. Sterile surgical drape 12 can be formed from many appropriate materials or combinations of materials, including, but not limited to, nonwoven materials, films, and woven materials. Flexible sterile surgical drape 12 is sterile, remains sterile, and is used to maintain a sterile field during surgery.

Flexible thermal device 14 may incorporate an active thermal heating or cooling device, but may also be a passive thermal barrier or insulator. Possible active thermal mediums that may be used in combination with flexible thermal device 14 include, but are not limited to, electrical heating elements, thermoelectric heating or cooling elements, hot or cold liquids, hot or cold gases, and endothermic or exothermic chemical reactants. Flexible thermal device 14 may also include a recyclable hot or cold gas heating or cooling system, which recirculates hot or cold gas through channels in flexible thermal device 14, and does not exhaust the heated or cooled gas to the environment.

In addition to an active thermal heating or cooling device, flexible thermal device 14 includes exterior surface 15 that contacts the patient when drape 10 is in use. Exterior surface 15 is typically a woven fabric, but may also be made from a nonwoven material or film. When exterior surface 15 is a woven fabric, it may be used to exhaust hot or cold gas from channels in flexible thermal device 14 onto a patient covered by flexible thermal device 14.

Sterile surgical drape 12 and flexible thermal device 14 are connected at a predetermined location by connection 16. Connection 16 may be made by many appropriate fastening techniques, including, but not limited to, sonic welding, laser welding, adhesive attachment, heat sealing, hook and loop systems, plastic fixtures such as track bars or snaps, and zippers. In addition, connection 16 may be made by the material of sterile surgical drape 12 or flexible thermal device 14, such as by melting or softening the material. Connection 16 may be made at any desired location or locations, including but not limited to at a point, along a line or edge, or continuously at the interface between sterile surgical drape 12 and flexible thermal device 14. Connection 16 may also be used to form passageways for carrying a fluid (liquid or gaseous) between sterile surgical drape 12 and flexible thermal device 14, or a compartment for holding an electrical resistance heating element or manipulably rupturable compartment containing heat-generating or heat-absorbing reactants.

In operation, sterile surgical-thermal drape 10 is prepared for use by medical personnel, who first remove it from appropriate packaging and then place it on the desired patient surface with exterior surface 15 of flexible thermal device 14 in contact with the patient. Next, the appropriate connections are made between active heating or cooling equipment and flexible thermal device 14 so that device 14 provides appropriate heating or cooling. It should be noted that sterile surgical drape 12 is not in contact with any unsterilized surface or objects while connections to flexible thermal device 14 are made, thus maintaining the sterility of sterile surgical drape 12.

After all necessary connections have been made, sterile surgical-thermal drape 10 is positioned over a patient (not explicitly shown) with exterior surface 15 of flexible thermal device 14 in contact with the patient and sterile surgical drape 12 disposed outwardly from device 14. Surgical procedures may then be performed on exposed portions of the patient or through a fenestration in drape 10 (not explicitly shown) without risking inadvertent contamination of medical instruments or devices by contact with flexible thermal device 14. An incise may be used instead of a fenestration. An incise is typically a piece of translucent material that may be cut into a fenestration or opening of any desired size. For the purposes of the present invention, a fenestration or incise may be used interchangeably unless otherwise noted.

Figure 1B:
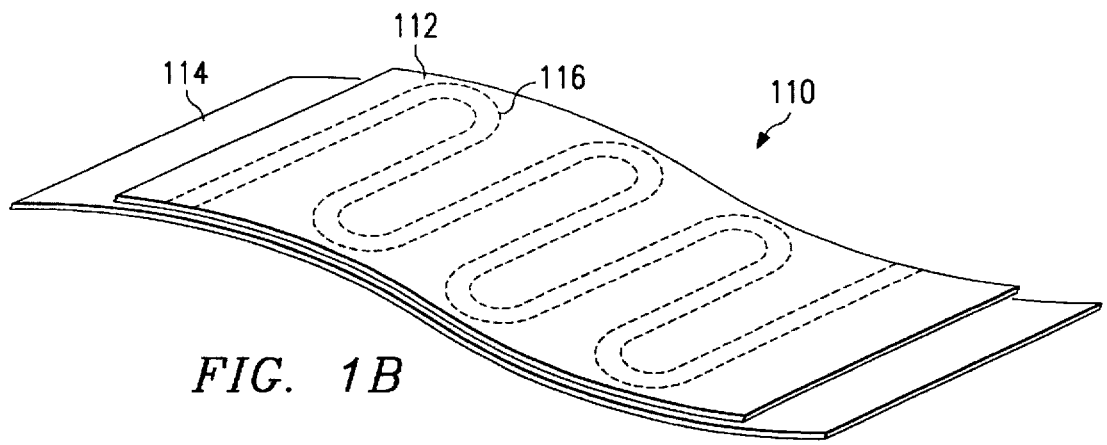

FIG. 1B shows sterile surgical-thermal drape 110 embodying concepts of the present invention. Drape 110 includes sterile surgical surface 112 and thermal surface 114, both of can be formed from many appropriate materials or combinations of materials, including, but not limited to, nonwoven materials, films, and woven materials. Sterile surgical surface 112 and flexible thermal surface 114 may be of identical size, or may have different shapes and sizes as shown in FIG. 1B. Drape 110 is sterile, remains sterile, and is used to maintain a sterile field during surgery.

Drape 110 incorporates an active thermal heating or cooling device or devices. Possible active thermal devices that may be used in combination with drape 110 include, but are not limited to, electrical heating elements, thermoelectric heating or cooling elements, hot or cold liquids, hot or cold gases, and endothermic or exothermic chemical reactants. As shown in FIG. 1B, passageways 116 are formed between sterile surgical surface 112 and thermal surface 114 by an appropriate method, such as by bonding, gluing, sonic welding, or melting the material of sterile surgical surface 112 or thermal surface 114. Instead of passageways, other thermal devices may be included between sterile surgical surface 112 and thermal surface 114, such as resistive heating elements or exothermic chemicals.

In operation, sterile surgical-thermal drape 110 is prepared for use by medical personnel, who first remove it from appropriate packaging and then place it on the desired patient surface with thermal surface 114 of drape 110 in contact with the patient. Next, the appropriate connections are made between active heating or cooling equipment and drape 110 so that drape 110 provides appropriate heating or cooling. It should be noted that sterile surgical surface 112 is not in contact with any unsterilized surface or objects while connections to drape 110 are made, thus maintaining the sterility of sterile surgical surface 112.

After all necessary connections have been made, drape 110 is positioned over a patient (not explicitly shown) with thermal surface 114 of drape 110 in contact with the patient and sterile surgical surface 112 disposed outwardly from drape 110. Surgical procedures may then be performed on exposed portions of the patient or through a fenestration in drape 110 (not explicitly shown) without risking inadvertent contamination of medical instruments or devices by contact with thermal surface 114.

One skilled in the art will recognize that sterile surgical-thermal drape 10 and drape 110 are exemplary. An embodiment of the present invention may incorporate features of either sterile surgical-thermal drape 10 or drape 110 in order to provide thermal regulatory capability during surgery while maintaining a sterile operating field.

Figure 2A:
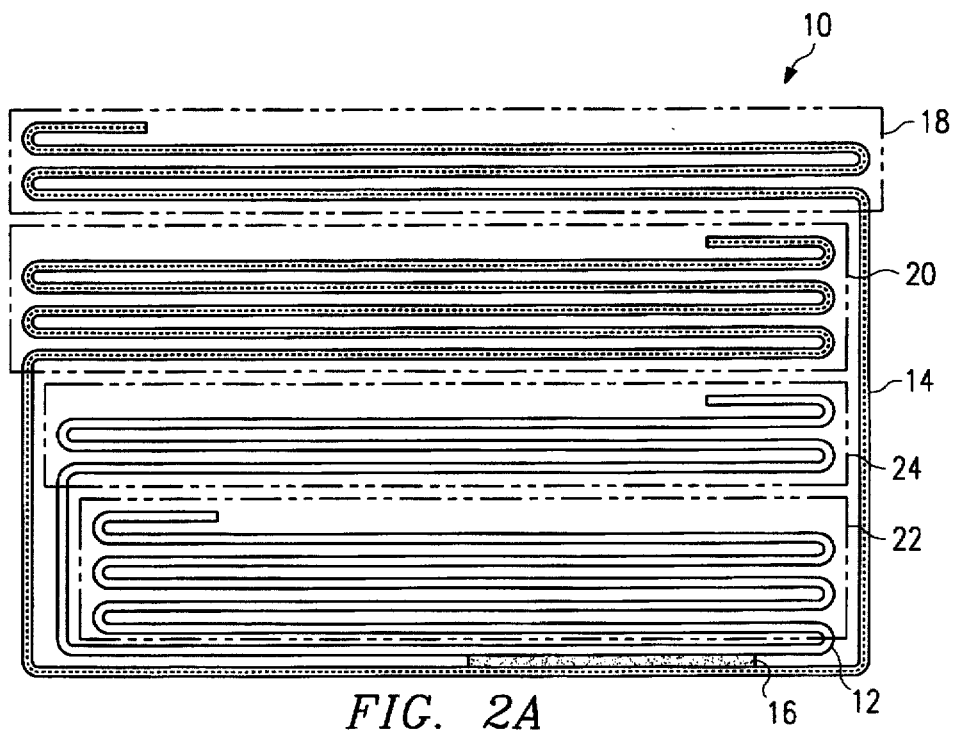
FIGS. 2A and 2B show sterile surgical-thermal drapes showing folding and attachments in accordance with the teachings of the present invention.

FIG. 2A illustrates sterile surgical-thermal drape 10 after folding, according to the teachings of the present invention. Thermal head section 18 and thermal feet section 20 are externally configured as shown. Surgical drape head section 22 and surgical drape feet section 24 are internally configured as shown, enclosed by flexible thermal device 14. This configuration of drape 10 allows sterile surgical drape 12 to be maintained in a sterile environment, and also provides access to flexible thermal device 14 so that it may be prepared for use, such as by attachment to an external heating or cooling system.

In operation, sterile surgical-thermal drape 10 is applied by first unfolding thermal device head section 18 and thermal device feet section 20. At this stage, sterile surgical drape 12 is still completely contained within a sterile environment. Because flexible thermal device 14 does not need to be maintained in a sterile environment, subsequent preparatory steps may be performed on device 14 after placing sterile surgical-thermal drape 10 on a non-sterile surface. Surgical drape head section 22 and surgical drape feet section 24 may then be unfolded and placed on top of thermal device head section 18 and thermal device feet section 20. Although the surface of sterile surgical drape 12 that is in contact with flexible thermal device 14 is no longer sterile, the opposite surface of sterile surgical drape 12 remains sterile. Sterile surgical-thermal drape 10 thus maintains a sterile field and allows for heating or cooling a patient.

Figure 2B:
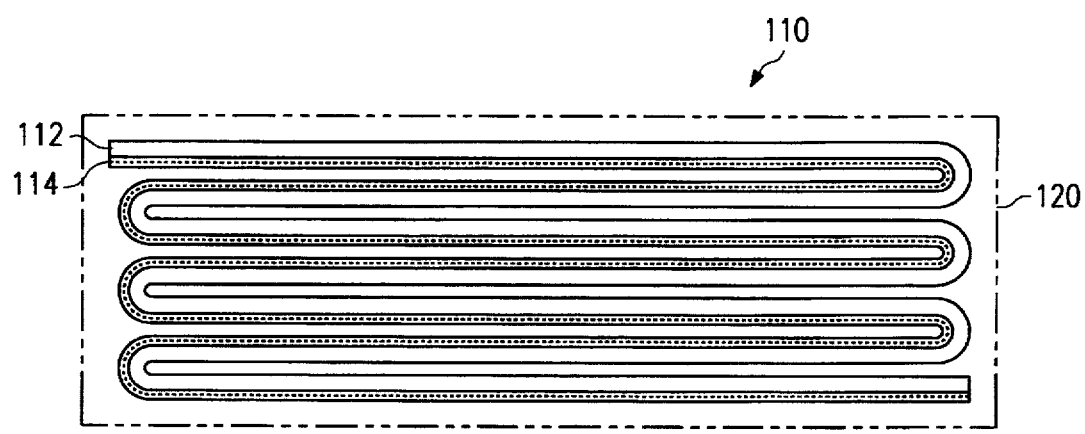

FIG. 2B illustrates drape 110 after folding, according to the teachings of the present invention. Drape 110 is contained within packaging 120. Because sterile surgical surface 112 and thermal surface 114 are coextensive with each other, all of drape 110 is sterilized and maintained within packaging 120. In operation, drape 110 is applied by opening packaging 120 and unfolding drape 110. At this stage, the sterility of sterile surgical surface 112 is maintained by placing drape 110 on thermal surface 114 while any preparatory steps are performed on drape 110. After drape 110 has been prepared, it is placed on the patient (not explicitly shown) with thermal surface 114 in contact with the patient and sterile surgical surface 112 facing the medical personnel performing the medical procedures. Drape 110 thus maintains a sterile field and allows for heating or cooling a patient.

Figure 3:
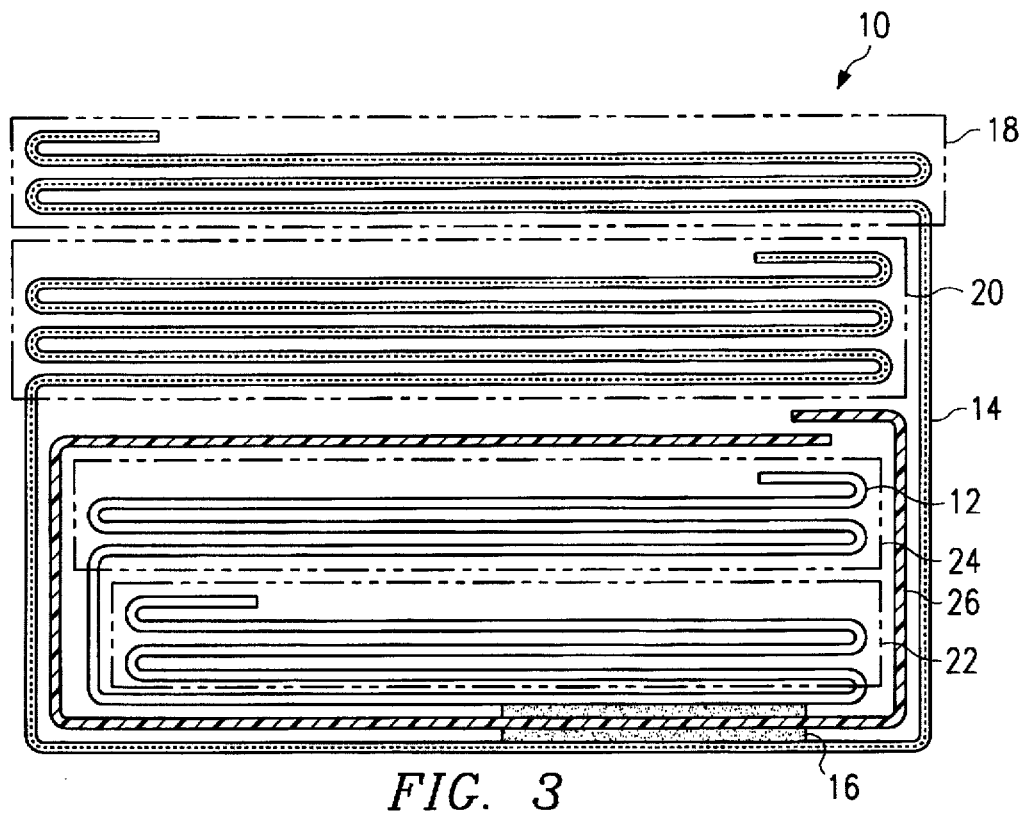
FIG. 3 depicts a sterile surgical-thermal drape showing folding, attachments, and barrier in accordance with teachings of the present invention.

FIG. 3 illustrates an alternate embodiment of sterile surgical-thermal drape 10 after folding embodying concepts of the present invention. Drape 10 in FIG. 3 includes barrier 26 that is used to help maintain the sterility of sterile surgical drape 12. Thermal head section 18 and thermal feet section 20 are externally configured as shown. Surgical drape head section 22 and surgical drape feet section 24 are internally configured as shown, enclosed by flexible thermal device 14. In addition, barrier 26 attaches by connection 16 between sterile surgical drape 12 and flexible thermal device 14. Barrier 26 may be made of many materials that act as a barrier to moisture, bacteria, and viruses, such as, for example, a thermoplastic film. Barrier 26 can either be folded around sterile surgical drape 12 or it may encase sterile surgical drape 12 and be hermetically sealed by many appropriate methods, including, but not limited to, welding, laser welding, adhesive attachment, and heat sealing. In operation, barrier 26 remains sealed until sterile surgical drape 12 is used.

Figure 4A:
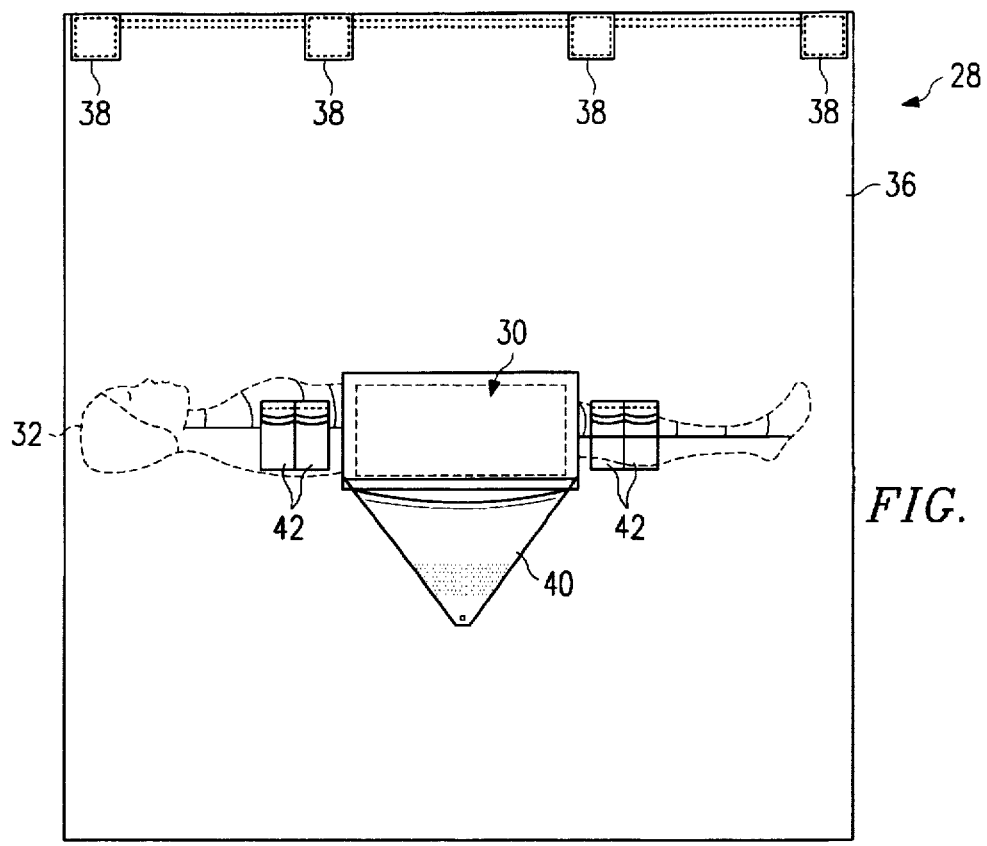
FIG. 4A and 4B illustrate the use of a sterile surgical-thermal drape with an incise of the present invention.
Figure 4B:
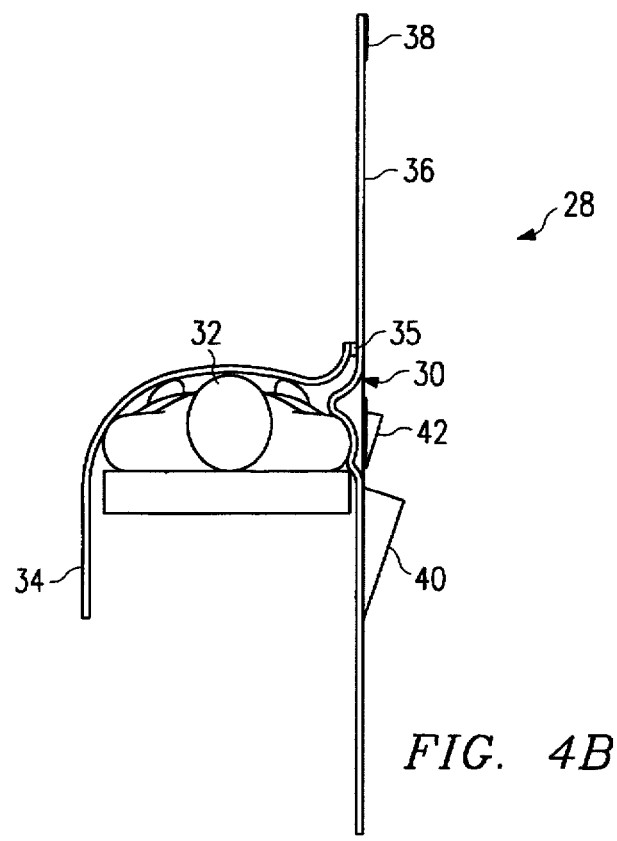

FIGS. 4A and 4B illustrate the use of sterile surgical-thermal drape 28 having fenestration/incise 30 in accordance with teachings of the present invention. As shown in FIG. 4A, fenestration/incise 30 is an area in sterile surgical-thermal drape 28 that allows medical personnel to access patient 32 while maintaining the integrity of a sterile field. Fenestration/incise 30 may be of many predetermined sizes and may be in many predetermined locations in drape 28, such that sterile surgical-thermal drape 28 can be used in connection with many medical procedures. As shown in FIG. 4A, fenestration/incise 30 is configured in drape 28 for use in hip surgery on patient 32. A sterile adhesive may be applied around the periphery of fenestration/incise 30 to secure the location of fenestration/incise 30 on patient 32.

FIG. 4B shows an alternate view of the use of sterile surgical-thermal drape 28 in FIG. 4A looking toward the head of patient 32. Drape 28 includes flexible thermal device 34 attached to sterile surgical drape 36 along a line that is parallel with patient 32. The location of fenestration/incise 30 is indicated in FIG. 4B, but fenestration/incise 30 is not explicitly shown in FIG. 4B.

In operation, sterile surgical-thermal drape 28 is suspended from overhead and adjacent to patient 32 by hanging supports 38 as shown in FIGS. 4A and 4B. Sterile surgical drape 36 hangs vertically, and flexible thermal device 34 couples to drape 36 along connection 35 that is parallel with patient 32. Flexible thermal device 34 is draped over patient 32. Fenestration/incise 30 is placed adjacent to the area to which access is required during surgery, i.e., the hip of patient 32. Adhesive may be used to attach incise 30 to a specific location on patient 32. If fenestration/incise 30 is an incise, medical personnel may remove by cutting any desired sections of fenestration/incise 30. Flexible thermal device 34 does not extend into the area defined by incise 30.

As shown in FIGS. 4A and 4B fluid pocket 40 may also be provided with drape 28 to catch any fluids that pass through fenestration/incise 30. Drape 28 may also include surgical instrument pockets 42 to hold sterile surgical instruments or devices that are required to perform the surgical procedures.

Figure 5:
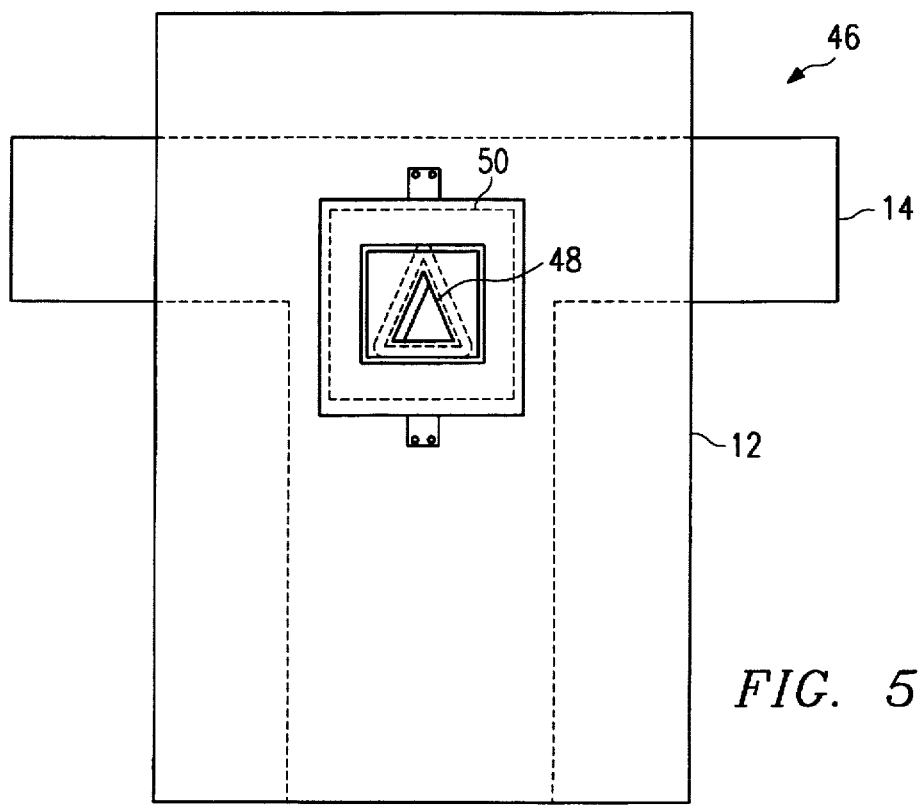
FIG. 5 shows a sterile surgical-thermal drape with a fenestration suitable for use when performing a cesarean section embodying concepts of the present invention.

FIG. 5 shows sterile surgical-thermal drape 46 embodying concepts of the present invention that may be used when performing a cesarean section birth procedure on a patient (not explicitly shown). Drape 46 includes flexible sterile surgical drape 12 and flexible thermal device 14. Fenestration/incise 48 in sterile surgical drape 12 is located in the area that the cesarean section is to be performed. Adhesive may be applied about the periphery of fenestration/incise 48 to secure surgical-thermal drape 46 to the patient (not explicitly shown).

Fluid pocket 50 is used to catch any fluids that pass through fenestration/incise 48. Flexible thermal device 14 extends over the areas shown in FIG. 5 to provide heating or cooling to a patient, but does not extend over the area defined by fenestration/incise 48. Sterile surgical-thermal drape 46 in FIG. 5 provides for appropriate heating or cooling of a patient while maintaining a sterile field. As previously noted, one skilled in the art will recognize that sterile surgical-thermal drape 46 may incorporate features of drape 110, with sterile surgical surface 112 and thermal surface 114 forming coolant passageways or enclosing active thermal elements, without departing from the scope and spirit of the present invention.

Figure 6:
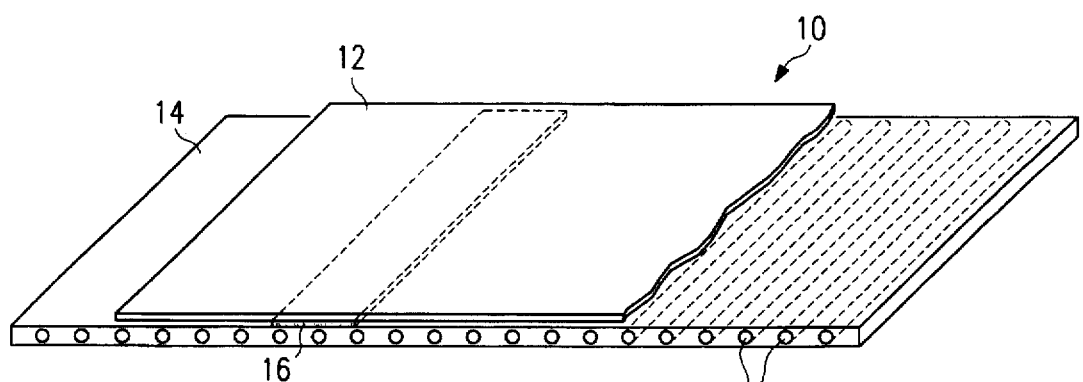
FIG. 6 illustrates a sterile surgical-thermal drape in accordance with the present invention having conducting passageways for carrying a fluid.

FIG. 6 illustrates another embodiment of the present invention and shows sterile surgical-thermal drape 10 having conducting passageways 54 in flexible thermal device 14 for carrying a fluid. Conducting passageways 54 may be formed in flexible thermal device 14 by many appropriate techniques, including, but not limited to, welding or glueing of individual laminae of flexible thermal device 14, extrusions within flexible thermal device 14, and adhesion to flexible thermal device 14. Additionally, fenestrations like those shown in FIGS. 4A, 4B, and 5 may be provided in drape 10 of FIG. 6.

In operation of surgical-thermal device 10 in FIG. 6, a manifold (not explicitly shown) is connected to a coolant/heating fluid circulation path (not explicitly shown) and to conducting passageways 54 in flexible thermal device 14. Alternatively, passageways 54 may be formed as a series of connected passages having a limited number of inputs and outputs. A coolant or heating fluid may be circulated through conducting passageways 54, thus providing cooling or heating to a patient. The fluid used in thermal device 14 may be either a liquid or a gas. As previously noted, one skilled in the art will recognize that the embodiment of sterile surgical-thermal drape 10 shown in FIG. 6 may also incorporate features of drape 110, with sterile surgical surface 112 and thermal surface 114 forming coolant passageways or enclosing active thermal elements, without departing from the scope and spirit of the present invention.

Figure 7:
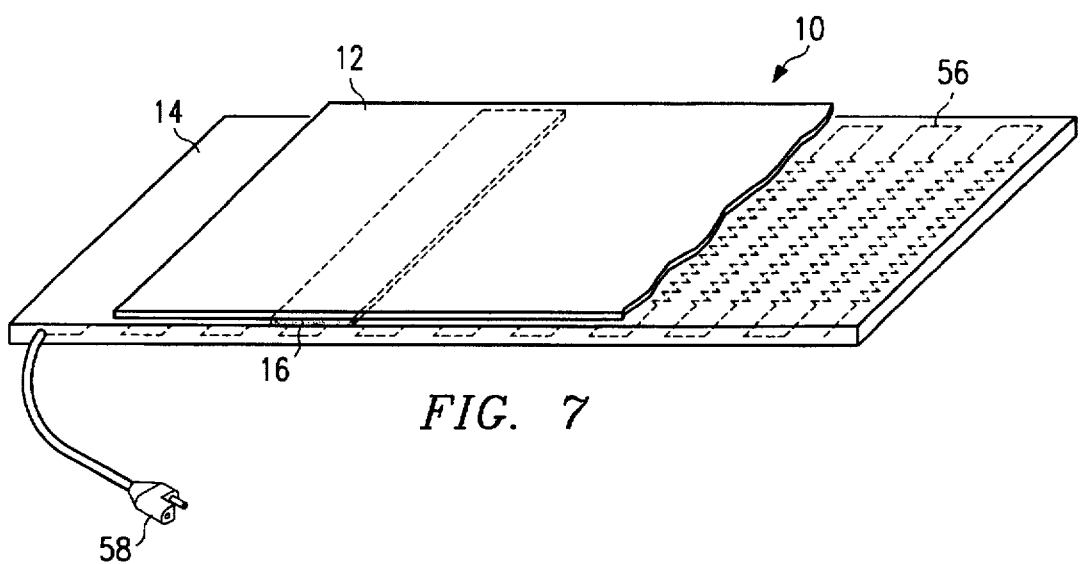
FIG. 7 shows a sterile surgical-thermal drape in accordance with the present invention having resistive heating elements.

FIG. 7 shows another embodiment of sterile surgical-thermal drape 10 of the present invention having resistive heating elements 56. Drape 10 in FIG. 7 includes sterile surgical drape 12, flexible thermal device 14, and connection 16. Resistive heating elements 56 may be fabricated from many appropriate materials. Resistive heating elements 56 are enclosed within flexible thermal device 14 by many appropriate methods, including, but not limited to, extrusion within flexible thermal device 14 and adhesion to flexible thermal device 14.

In operation of drape 10 in FIG. 7, power cord 58 couples to an appropriate power source to provide electrical energy to resistive heating elements 56. The power source may provide alternating or direct current power at many appropriate voltages and frequencies. Applying current to resistive heating elements 56 causes heat to be generated, thus providing heating to a patient. It is noted that thermoelectric elements may also be used in lieu of resistive heating elements 56, such that sterile surgical-thermal drape 10 may be used to provide cooling as well as heating to a patient. As previously noted, one skilled in the art will recognize that the embodiment of sterile surgical-thermal drape 10 shown in FIG. 7 may incorporate features of drape 110, with sterile surgical surface 112 and thermal surface 114 forming coolant passageways or enclosing active thermal elements, without departing from the scope and spirit of the present invention.

Figure 8:
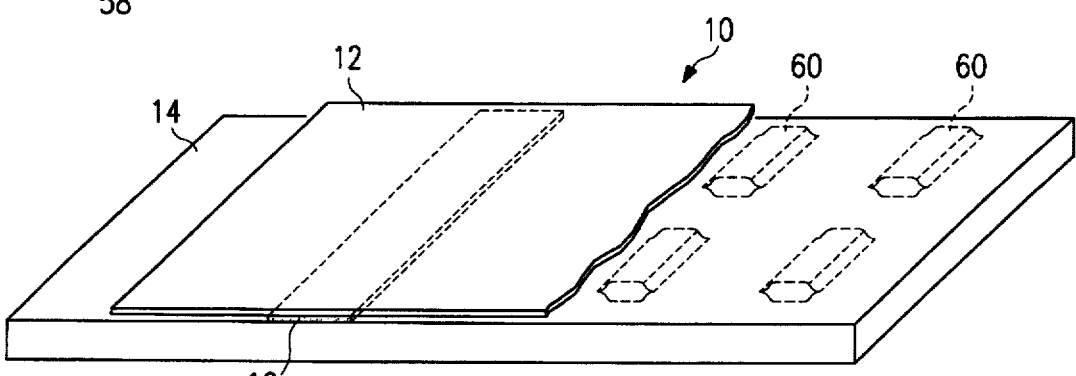
FIGS. 8 and 8A illustrate a sterile surgical-thermal drape in accordance with the present invention having thermal producing manipulably rupturable chambers.
Figure 8A:
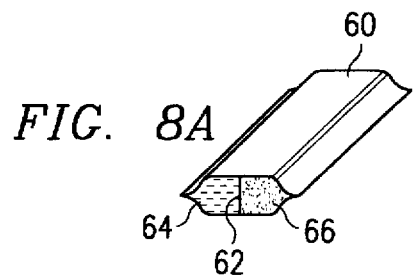

FIGS. 8 and 8A illustrate another embodiment of sterile surgical-thermal drape 10 having manipulably rupturable chambers 60. Drape 10 in FIG. 8 includes sterile surgical drape 12, flexible thermal device 14, and connection 16. Manipulably rupturable chambers 60 may be formed by many appropriate means, including, but not limited to, welding or glueing of individual laminae of flexible thermal device 14, extrusion within flexible thermal device 14, and adhesion to flexible thermal device 14.

As shown in FIG. 8A, manipulably rupturable chamber 60 includes manipulably rupturable membrane 62 and chemical reactants 64 and 66. Chemical reactants 64 and 66 create an exothermic or endothermic chemical reaction when mixed, such that rupturing manipulably rupturable membrane 62 causes chemical reactants 64 and 66 to mix and either generate (exothermic) or absorb (endothermic) heat.

In operation of drape 10 in FIGS. 8 and 8A, manipulably rupturable chamber 60 in flexible thermal device 14 of drape 10 is compressed or agitated until manipulably rupturable membrane 62 is ruptured, thus causing chemical reactants 64 and 66 to mix. After chemical reactants 64 and 66 mix, they either generate or absorb heat, thus heating or cooling a patient. As previously noted, one skilled in the art will recognize that the embodiment of sterile surgical-thermal drape 10 shown in FIG. 8 may incorporate features of drape 110, with sterile surgical surface 112 and thermal surface 114 forming fluid passageways or enclosing active thermal elements, without departing from the scope and spirit of the present invention.

Figure 9A:
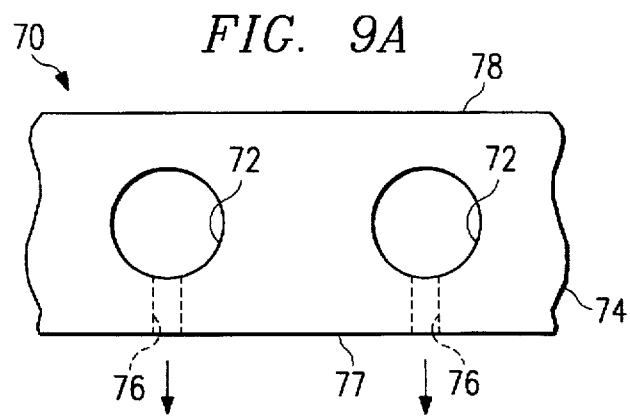
FIGS. 9A and 9B show sterile surgical-thermal drapes with active air circulation embodying concepts of the present invention.
Figure 9B:
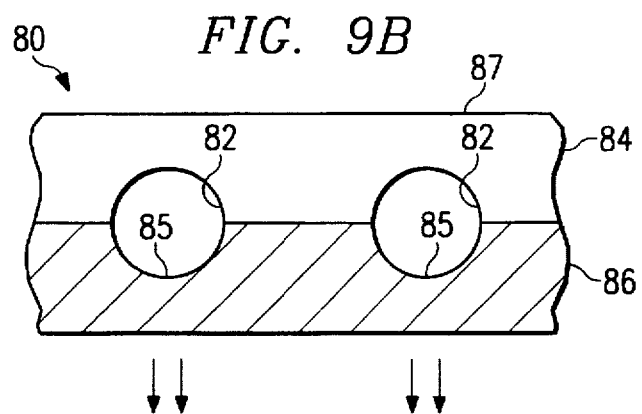

FIGS. 9A and 9B show a cross-section of a sterile surgical-thermal drape with active air circulation embodying concepts of the present invention. In FIG. 9A sterile surgical thermal drape 70 includes fluid passageways 72 in thermal device 74. Perforations 76 are formed in thermal device 74, such as by puncturing, cutting, machining, or other suitable method to provide access to passageways 72. Perforations 76 allow a fluid in fluid passageways 70 to exit in the direction shown by the arrows in FIG. 9A. Typically, surface 77 of sterile surgical drape 70 contacts the patient so that the patient receives appropriate convection heating or cooling from thermal device 74. A surgical surface or surgical drape is preferably disposed on surface 78 of sterile surgical drape 70 opposite surface 77 to provide a sterile workplace.

In operation, a fluid, such as air, is made to flow through fluid passageways 72. The pressure required to force the fluid through fluid passageways 72 raises the pressure inside of fluid passageways 72 to a pressure greater than that external to thermal device 74. Thus, the fluid in fluid passageways 72 will exit through perforations 76 in the direction shown by the arrows in FIG. 9A, which allows radiant heat to be used to control the body temperature of a patient (not explicitly shown).

Similarly, sterile surgical thermal drape 80 in FIG. 9B includes fluid passageways 82 in thermal device 84. Woven material 86 is attached to thermal device 84 and forms portion 85 of fluid passageways 82. Woven material 86 allows fluid in fluid passageways 82 to exit in the direction shown by the arrows in FIG. 9B. A surgical surface or surgical drape is preferably disposed on surface 87 opposite woven material 86.

In operation, a fluid, such as air, is made to flow through fluid passageways 82. The pressure required to force the fluid through fluid passageways 82 raises the pressure inside of fluid passageways 82 to a pressure greater than that external to thermal device 84. Thus, the fluid in fluid passageways 82 will exit through woven material 86 in the direction shown by the arrows in FIG. 9B. This flow allows radiant cooling to be used to control the body temperature of a patient (not explicitly shown).

One skilled in the art will recognize that fluid passageways 72 and 82 in FIGS. 9A and 9B, respectively, may be used to carry heated gas or liquids, and that such heated gasses or liquids may be used to control the body temperature of a patient. Likewise, a porous non-woven material may be used in place of woven material 86 in sterile surgical thermal drape 80 without departing from the spirit or scope of the present invention.

Figure 10:
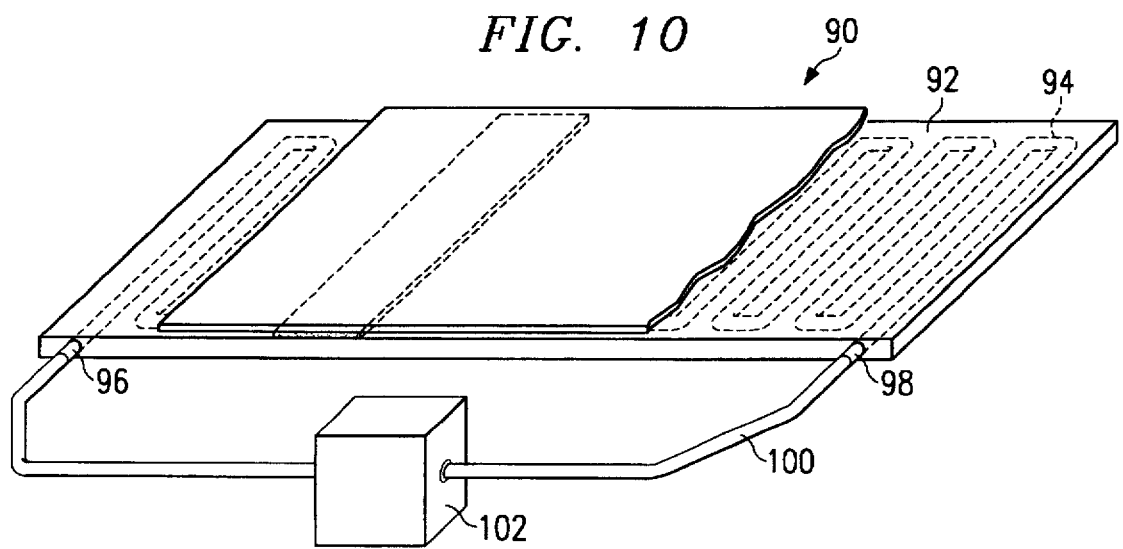
FIG. 10 shows a thermal drape with a recirculation system.

FIG. 10 shows thermal drape 90 with recirculation system 102. Thermal drape 90 has a first surface and a second surface, and includes fluid passageway 94 having entrance 96 and exit 98. Fluid passageway 94 may have many suitable configurations, such as to provide heating or cooling to specific portions of a patient, or to allow a fenestration or incise to be placed in thermal drape 90. One surface of thermal drape 90 may be sterilized to allow surgical procedures to be performed. Likewise, a sterile surgical drape may be attached to one surface of thermal drape 90. External fluid passageway 100 couples to entrance 96, exit 98, and recirculation system 102. External fluid passageway 100 may be many suitable materials that are operable to conduct a hot or cold fluid, such as a polymer or a plastic. Entrance 96 and exit 98 may include many suitable couplings that are operable to connect fluid passageways 94 to external fluid passageway 100. Recirculation system 102 is operable to circulate a fluid through fluid passageways 94, and may be operable to provide heating or cooling to the fluid.

In order for recirculation system 102 to be operable to circulate a fluid through fluid passageways 94, the entire fluid flow path must be airtight, including fluid passageway 94, external fluid passageway 100, and the connection between external fluid passageway 100 and fluid passageway 94 at entrance 96 and exit 98.

In operation, recirculation system 102 heats or cools a fluid material, such as a liquid or a gas, and forces the fluid through external fluid passageway 100 and fluid passageway 94. The fluid is not discharged to the atmosphere, which improves the efficiency of the system and provides other benefits that are readily apparent to one skilled in the art.

The present invention thus provides a device and method that may be used to maintain a sterile surgical field while providing sufficient heat to a patient to prevent the onset of hypothermia. A device incorporating concepts of the present invention may be used to controllably provide heat to a patient undergoing surgery while maintaining the sterile environment needed to safely perform surgery. A method incorporating concepts of the present invention provides a surgical-thermal draping system that maintains the sterility of the surgical drape while allowing operating room personnel to handle and prepare the surgical-thermal draping system for use in surgery.

Although the present invention has been described in detail, it should be understood that various changes, substitutions, and alterations can be made hereto without departing from the spirit and scope of the invention as defined by the appended claims.

What is claimed is:

1. A sterile surgical-thermal drape comprising:
   a sterile surgical drape for use during surgery operable to maintain a sterile surgical field; and
   a thermal device attached to the sterile surgical drape operable to regulate the body temperature of a patient, wherein the thermal device is operable to provide at least one of convective heating and cooling to the patient by directing a hot or cold fluid towards the patient, the thermal device comprising a fluid passageway operable to conduct at least one of a gas and a liquid, wherein the thermal device further comprises a woven material, and wherein the woven material forms a portion of a sidewall of the fluid passageway.

2. A sterile surgical-thermal drape comprising:
   a sterile surgical drape for use during surgery operable to maintain a sterile surgical field;
   a fluid passageway that is operable to conduct at least one of a gas and a liquid;
   a thermal device attached to the sterile surgical drape operable to regulate the body temperature of a patient and wherein the thermal device is operable to provide at least one of convective heating and cooling to the patient, wherein the thermal device further comprises a woven material, and wherein the woven material forms a portion of a sidewall of the fluid passageway;
   one of a fenestration and an incise for exposing a portion of the patient's body during surgery; and
   a barrier attached between the sterile surgical drape and the thermal device and enclosing the sterile surgical drape for maintaining the sterility of the sterile surgical drape.

3. The sterile surgical-thermal drape of claim 1 wherein the sterile surgical drape further comprises one of a fenestration and an incise for exposing a portion of the patient's body.

4. The sterile surgical-thermal drape of claim 1 further comprising a barrier attached between the sterile surgical drape and the thermal device and enclosing the sterile surgical drape for maintaining the sterility of the sterile surgical drape.

5. The sterile surgical-thermal drape of claim 3 further comprising a fluid pocket operable to receive fluids passing through the one of a fenestration and an incise.

6. The sterile surgical-thermal drape of claim 2 further comprising a fluid pocket operable to receive fluids passing through the one of a fenestration and an incise.

* * * * *